us

United States Patent
Fung et al.

(10) Patent No.: US 8,027,939 B2
(45) Date of Patent: Sep. 27, 2011

(54) AUTOMATIC LABELER ASSIGNMENT USING A MODEL BUILT FROM MULTI-LABELER DATA

(75) Inventors: Glenn Fung, Madison, WI (US); Romer E. Rosales, Downingtown, PA (US); Jennifer G. Dy, Framingham, MA (US); Yan Yan, Jamaica Plain, MA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 12/893,008

(22) Filed: Sep. 29, 2010

(65) Prior Publication Data
US 2011/0071967 A1 Mar. 24, 2011

Related U.S. Application Data

(63) Continuation-in-part of application No. 11/877,066, filed on Oct. 23, 2007.

(60) Provisional application No. 61/246,673, filed on Sep. 29, 2009, provisional application No. 60/856,160, filed on Nov. 2, 2006.

(51) Int. Cl.
*G06F 15/18* (2006.01)
*G06K 9/00* (2006.01)
*G06K 9/62* (2006.01)

(52) U.S. Cl. .......................... 706/12; 382/128; 382/155

(58) Field of Classification Search ................. None
See application file for complete search history.

(56) References Cited

U.S. PATENT DOCUMENTS

| | | | | |
|---|---|---|---|---|
| 5,768,333 | A * | 6/1998 | Abdel-Mottaleb | 378/37 |
| 5,857,030 | A * | 1/1999 | Gaborski et al. | 382/132 |
| 6,125,194 | A * | 9/2000 | Yeh et al. | 382/132 |
| 7,474,775 | B2 * | 1/2009 | Abramoff et al. | 382/128 |
| 7,783,585 | B2 | 8/2010 | Sabe et al. | |
| 2005/0187892 | A1 | 8/2005 | Goutte et al. | |
| 2008/0301077 | A1 | 12/2008 | Fung et al. | |
| 2009/0125461 | A1 | 5/2009 | Qi et al. | |

OTHER PUBLICATIONS

Lam et al.; "Toward Optimal Labeling Strategy under Multiple Unreliable Labelers"; 2005; American Assoication for Articial Intelligence; pp. 1-6.*
Dawid et al.; "Maximum Likelihood Estimation of Observer Error-Rates Using the EM Algorithm"; 1979; Journal of the Royal Statistical Society. Series C (Applied Statistics), vol. 28, No. 1; pp. 20-28.*
Brodley et al.; "Identifying and Eliminating Mislabeled Training Instances"; 1996; Thirteenth National Conference on Artificial Intelligence; pp. 799-805 (1-7).*
Richardson et al.; "Learning with Knowledge from Multiple Experts"; 2003; Proceedings of the Twentieth International Conference on Machine Learning (ICML-2003); pp. 1-8.*

(Continued)

*Primary Examiner* — Jeffrey A Gaffin
*Assistant Examiner* — Stanley K Hill
(74) *Attorney, Agent, or Firm* — Joshua B. Ryan

(57) ABSTRACT

A method, including receiving multi-labeler data that includes data points labeled by a plurality of labelers; building a model from the multi-labeler data, wherein the model includes an input variable that corresponds to the data points, a label variable that corresponds to true labels for the data points, and variables for the labels given by the labelers; and executing the model, in response to receiving new data points, to determine a level of expertise of the labelers for the new data points.

17 Claims, 4 Drawing Sheets

OTHER PUBLICATIONS

Jin et al.; "Learning with Multiple Labels"; 2002; Advances in Neural Information Processing Systems (NIPS); pp. 1-8.*

Donmez et al.; "Efficiently learning the accuracy of labeling sources for selective sampling"; 2009; ACM New York; pp. 259-267.*

Boutell, Matthew, et al., "Learning multi-label scene classification", Pattern Recognition 37 (2004) 1757-1771.

Zhu, Shenghuo, "Multi-labelled Classification Using Maximum Entropy Method", ACM, 2005 (pp. 1-8).

Ghamrawi, et al., Collective Multi-Label Classification ACM, 2005,(pp. 195-200.

Donmez, et al., A Probabilistic Framework to Learn From Multiple Annotators With Time-Varying Accuracy, cs.cmu.edu, 2010, pp. 1-12.

Taskar, et al., Max-Margin Markov Networks, MIT Press, 2003 (pp. 1-8).

Lam, et al., Toward Optimal Labeling Strategy Under Multiple Unreliable Labelers, American Association for Artifical Intelligence, Dec. 1, 2005 (pp. 1-6).

Richardson, et al., Learning With Knowledge From Multiple Experts, Proceedings of the Twentieth International Conference on Machine Learning. AAAI Press, 2003 (pp. 1-8).

Donmez, et al., Efficiently Learning the Accuracy of Labeling Sources for Selective Sampling, ACM, 2009 (pp. 259-268).

Richardson, et al., Learning With Knowledge From Multiple Experts, In Proceedings of the Twentieth International Conference on Machine Learning, 2003. 8 Pages.

Brodley, et al., Identifying and Eliminating Mislabeled Training Instances, In Thirteenth National Conference on Artifical Intelligence, Aug. 1996. 7 Pages.

Dawid, et al., "Maximum Likelihood Estimation Observer Error-Rates Using EM Algorithm", 2005, American Association for Artificial Intelligence, pp. 1-6.

Jin, et al., "Learning with Multiple Labels", 2002, Advances in Neural Information Processing Systems (NIPS), pp. 1-8.

* cited by examiner

AUTOMATIC LABELER ASSIGNMENT USING A MODEL BUILT FROM MULTI-LABELER DATA

CROSS-REFERENCE TO RELATED APPLICATIONS

This application claims priority under 35 U.S.C. §119 to U.S. Provisional Application No. 61/246,673, filed Sep. 29, 2009, the disclosure of which is incorporated by reference herein in its entirety.

This application is a continuation-in-part of U.S. patent application Ser. No. 11/877,066, filed Oct. 23, 2007, which claims priority to U.S. Provisional Application No. 60/856,160, filed Nov. 2, 2006, the disclosures of which are incorporated by reference herein in their entireties.

BACKGROUND OF THE INVENTION

1. Technical Field

The present invention relates to modeling data that has been processed by multiple labelers, and more particularly, to producing labeler error/accuracy estimates and simultaneously building a classifier from multi-labeler data.

2. Discussion of the Related Art

In many real-life settings, something has to be learned from data. For example, the "thing" to be learned may be "What structures in a set of medical images (the data) are indicative of cancer and thus candidates for biopsy?" This learning may be accomplished with a supervised learning algorithm that analyzes the data to produce a classifier that identifies the biopsy candidates.

In general, the data to be learned is labeled by several experts. One reason why several labelers are needed is the lack of a golden ground-truth for many real-life settings. However, depending on the setting, there may be a large variance in the experts' scores that can lead to low overall agreement. For example, radiologists specialized in heart images are better at labeling lesions of the heart compared to radiologists with lung expertise, who on the other hand, label instances of lung diseases better.

Several machine learning-based algorithms have been developed that can learn concepts in the presence of simultaneous labels from a group of experts. It has been shown that this class of algorithm can learn the concept better than traditional methods when taking into account all the labels at the same time. However, this class of algorithm assumes that the reliability of labelers is the same across all data.

SUMMARY OF THE INVENTION

In an exemplary embodiment of the present invention, a method is provided that comprises: receiving multi-labeler data that includes data points labeled by a plurality of labelers; building a model from the multi-labeler data, wherein the model includes an input variable that corresponds to the data points, a label variable that corresponds to true labels for the data points, and variables for the labels given by the labelers; and executing the model, in response to receiving new data points, to determine a level of expertise of the labelers for the new data points, wherein the method is performed using a processor.

The method further comprises assigning the new data points to a particular labeler for labeling based on the labeler's level of expertise.

The labeler with the highest level of expertise is selected for the labeling of the new data points and wherein the highest level of expertise corresponds to the labeler's estimated ability to label the new data points more accurately than the other labelers.

The method further comprises classifying the new data points.

A new data point is classified by using less than all of the labels provided by the labelers.

The new data points are classified using a classifier that uses just the labels provided by the labelers as input.

The labelers include radiologists and the multi-labeler data includes radiological images.

The data points correspond to information extracted from regions of the images, the image regions including lesions, abnormalities or other elements of interest for patient treatment or diagnosis.

The labelers include medical experts and the multi-labeler data includes medical transcripts.

The data points correspond to information extracted from a medical transcript, the information including medical events, diagnosis, procedures underwent and overall state for a patient.

In an exemplary embodiment of the present invention, a system is provided that comprises: a memory device for storing a program; a processor in communication with the memory device, the processor operative with the program to: receive multi-labeler data that includes data points labeled by a plurality of labelers; build a model from the multi-labeler data, wherein the model includes an input variable x that corresponds to the data points, a label variable z that corresponds to true labels for the data points, and variables for the labels y given by each labeler t; and execute the model, in response to receiving new data points, to determine a level of expertise of the labelers for the new data points.

$p(y_i^{(t)}|x_i,z_i)$ is represented by $p(y_i^{(t)}|x_i,z_i)=N(y_i^{(t)};z_i,\sigma_t(x_i))$, wherein N is the number of data points input to the model and $\sigma_t(x)$ is an estimated error of a labeler for a particular data point.

$\sigma_t(x)$ is represented by $\sigma_t(x)=(1+\exp(-w_t^T x_i-\gamma_t))^{-1}$, wherein w is a vector (normally each component is a real number) and γ is a scalar (normally in the set of real numbers).

$p(y_i^{(t)}|x_i,z_i)$ is represented by $p(y_i^{(t)}|x_i,z_i)=(1-\eta_t(x))^{|y_i^{(t)}-z_i|}\eta_t(x)^{1-|y_i^{(t)}-z_i|}$, wherein N is the number of data points input to the model and $\eta_t(x)$ is an estimated accuracy of a labeler for a particular data point.

$\eta_t(x)$ is represented by $\eta_t(x)=(1+\exp(-w_t^T x_i-\gamma_t))^{-1}$, wherein w is vector and γ is a scalar.

$p(z_i, x_i)$ is represented by $p(z_i=1|x_i)=(1+\exp(-\alpha^T x_i-\beta))^{-1}$, wherein $\alpha^T$ is a vector and β is a scalar.

In an exemplary embodiment of the present invention, a system is provided that comprises: a memory device for storing a program; a processor in communication with the memory device, the processor operative with the program to: receive multi-labeler data that includes data points labeled by a plurality of labelers; build a model from the multi-labeler data, wherein the model includes an input variable x that corresponds to the data points, a label variable z that corresponds to true labels for the data points, and variables for the labels y given by each labeler t; and execute the model, in response to receiving new data points, to determine a level of expertise of the labelers for the new data points, wherein the model is represented by $$p(Y, Z \mid X) = \prod_i p(z_i \mid x_i) \prod_t p(y_i^{(t)} \mid x_i, z_i),$$

where $p(z_i, x_i)$ is a classifier for classifying new data points, and $p(y_i^{(t)} \mid x_i, z_i)$ is an error/accuracy estimator for determining labeler expertise.

DETAILED DESCRIPTION OF EXEMPLARY EMBODIMENTS

Disclosed herein, in accordance with an exemplary embodiment of the present invention, is a probabilistic model for learning a classifier from multiple labelers, where the reliability of the labelers varies according to each labeler and the data that the labeler observes. This model can not only learn a target concept by using all the available labels for each data point of a set of data points, but it also learns a predictive model for each labeler, wherein the predictive model assesses or scores the appropriateness of each labeler for a new set of data points that needs to be labeled. In this way, for a new set of data points, one can pick the expert with the best chance to label it correctly. This could save a considerable amount of time and money, since the new set of data points could be labeled by one (or a smaller number) of labelers.

Figure 1:
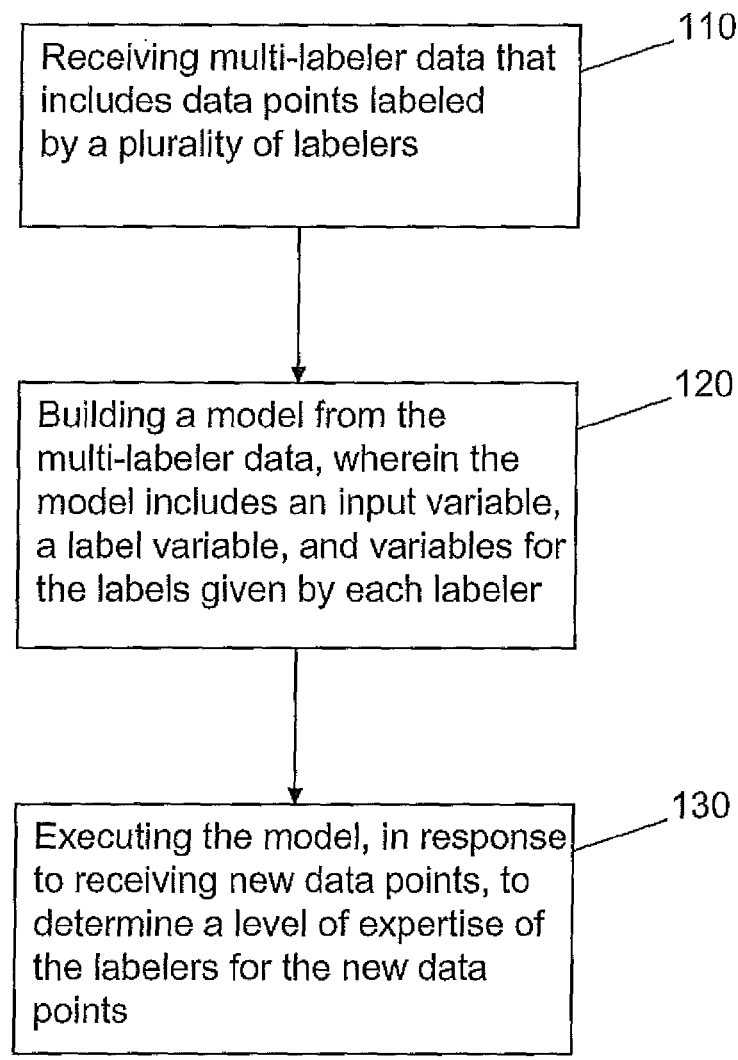
FIG. 1 is a flowchart illustrating an exemplary embodiment of the present invention.

FIG. 1 is a flowchart illustrating an exemplary embodiment of the present invention.

As shown in FIG. 1, multi-labeler data that includes data points labeled by a plurality of labelers is received (110). Such data may include a set computed tomography (CT) or magnetic resonance (MR) images for a patient, wherein the images include regions or volumes associated to a body tissue that are labeled to be tested for the presence of cancer. Each region or volume (e.g., data point) may or may not be labeled by all the labelers. Further, each region or volume may or may not be labeled correctly. In this case, the labelers are medical experts such as radiologists or doctors.

Formulaically, the multi-labeler data can be represented as follows. Given N data points $\{x_1, \ldots, x_N\}$, where $x_i \in R^D$, each labeled at most by T labelers/annotators, the label for the i-th data point given by annotator t is denoted as $y_i^{(t)} \in Y$. Since the labels from individual labelers may not be correct, the true (unknown) label for the i-th data point is denoted to be $z_i = Z$ (normally $Y \equiv Z$). For compactness, the matrices $X = [x_1^T; \ldots; x_N^T] \in R^{N \times D}$ and $Y = [y_1^{(1)}, \ldots, y_1^{(T)}; \ldots; y_N^{(1)}, \ldots, y_N^{(T)}] \in R^{N \times T}$ are set, where $(.)^T$ stands for the matrix response.

The multi-labeler data received in step 110 is not limited to medical image data. For example, the multi-labeler data can be medical text annotated/reviewed by multiple expert/non-expert personnel, genome sequences annotated using the results of scientific experiments or from the literature, or patient state given by various physician opinions.

A model is then built from the multi-labeler data (120). This model is the probabilistic model mentioned above. Once built with the training data X and Y of step 110, the probabilistic model can produce an estimate for the ground-truth $Z = [z_1, \ldots, z_N]^T$, a classifier for predicting the label z for new instances x, and a model of the annotators' expertise as a function of the input x. This will be discussed later.

The probabilistic model is represented formulaically as follows. Define the random variables $y^{(t)}$ over the space of labels Y, provided for labeler t, for $t = \{1, \ldots, T\}$. Define the random variables $x \in X$ and $z \in Z$ to represent input data points (observed) and unknown output respectively. Then, assume a probabilistic model over random variables x, y and z with a graphical model 200 as shown in FIG. 2.

Figure 2:
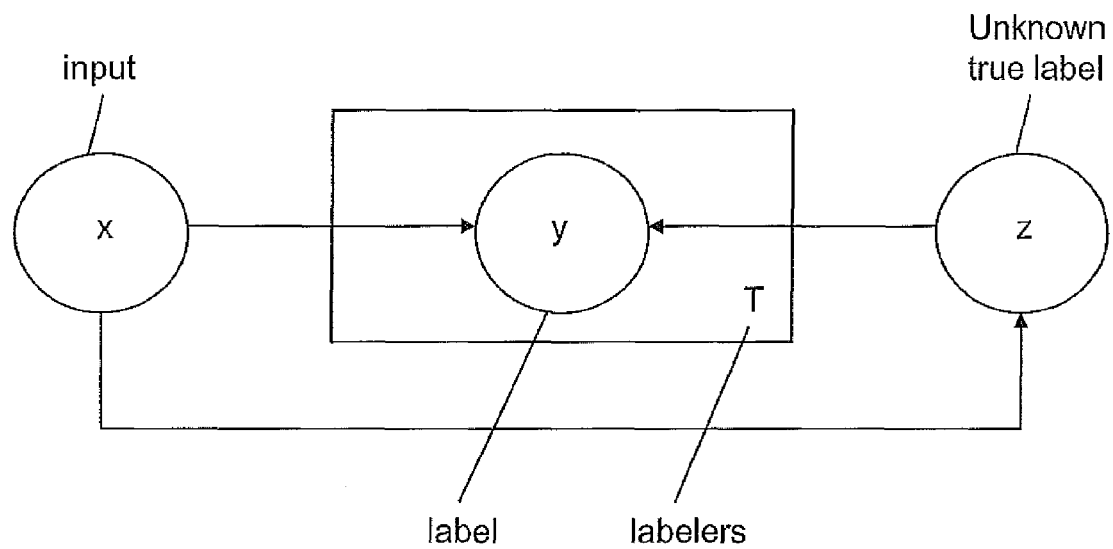
FIG. 2 is a graphical model of a probabilistic model according to an exemplary embodiment of the present invention.

In model 200 shown in FIG. 2, the annotation provided by the labeler t depends both on the unknown true label z but also on the (normally) observed input x. In other words, it is not assumed that the annotators are equally good (or bad) at labeling all the data; rather, it depends on what input they observe. As can be seen from model 200, the assumption is made that the labelers $t = \{1, \ldots T\}$ are independent given the input and the true label.

The joint conditional distribution (i.e., the probabilistic model) can be expressed as:

$$p(Y, Z \mid X) = \prod_i p(z_i \mid x_i) \prod_t p(y_i^{(t)} \mid x_i, z_i) \quad \text{(a)}$$

In the probabilistic model, following that discussed with reference to FIG. 2, the annotation provided by labeler t depends both on the unknown true label z but also on the (normally) observed input x. In other words, it is not assumed that the annotators are equally good (or bad) at labeling all the data; rather, it depends on what input they observe. As can be seen from the probabilistic model, the assumption is made that the labelers $t = \{1, \ldots, T\}$ are independent given the input and the true label. To further specify the probabilistic model, the form of the conditional probabilities are now defined.

Start with $p(y_i^{(t)} \mid x_i, z_i)$. This model assumes that each annotator t provides a noisy version of the true label z, $$p(y_i^{(t)} \mid x_i, z_i) = p(y_i^{(t)} \mid z_i) = (1 - \eta^{(t)})^{|y_i^{(t)} - z_i|} \eta^{(t)^{1 - |y_i^{(t)} - z_i|}},$$

with $Z \equiv Y = \{0, 1\}$. In this Bernoulli model, the parameter $\eta^{(t)}$ is the probability of labeler t to be correct (i.e., $y_i = z_i$). Another option is the Gaussian model, where every labeler is expected to provide a distorted version of the true label z, $p(y_i^{(t)} \mid z_i) = N(y_i^{(t)}; z_i, \sigma^{(t)})$. This Gaussian distribution associates a lower variance $\sigma^{(t)}$ to more consistently correct labelers compared to inconsistent labelers. Note that a distribution for continuous random variables is employed, which is more natural for regression than classification models (for y continuous). In these models, where it is assumed that $p(y_i^{(t)} \mid x_i, z_i) = p(y_i^{(t)} \mid z_i)$, the additional independence assumptions mean that the graphical model is Markov-equivalent to the model $x \to z \to \{y^{(t)}\}$.

These models are used as a base for considering cases where $p(y \mid x, z) \neq p(y \mid z)$. In real applications, it has been noticed that the quality of labels by annotators is not only a function of their expert level, but also of the type of data presented to them as well. For example, radiologists will have difficulty providing quality labels on blurry images. Additionally, some labelers will be more affected by blurry images than others and some labelers are more knowledgeable for some input types than others. In general, annotators will exhibit varying levels of expertise in different types of data. This may be particularly true for non-expert annotators.

To model this input dependent variability, the Gaussian model discussed above will be replaced with the following:

$$p(y_i^{(t)}|x_i,z_i) = N(y_i^{(t)}; z_i, \sigma_t(x_i)), \quad (1)$$

where the variance now depends on the input x and, is specific to each annotator t.

This allows us to take into account that the annotator t's accuracy/consistency may depend on the example observed. $\sigma_t(x)$ represents the variance function, in this case it represents how consistent the annotator is at providing the true label z. The main difference with the previously discussed model $p(y_i^{(t)}|z_i) = N(y_i^{(t)}; z_i, \sigma^{(t)})$ is that the variance is not fixed independently of the example observed. Thus, by using this model we get a model that has additional flexibility. This variance function is estimated from data.

Since the value of $y^{(t)}$ can only take the binary values 0/1, instead of allowing $\sigma_t(x)$ to be any value, it is constrained to be in the range between (0,1) by setting $\sigma_t(x)$ as a logistic function of $x_i$ and t:

$$\sigma_t(x) = (1 + \exp(-w_t^T x_i - \gamma_t))^{-1} \quad (2)$$

In other words, the variance for annotator t is a sigmoidal function with parameters $w_t$ and $\gamma_t$. These parameters can be estimated from training data.

To make sure that $\sigma_t(x)$ does not go to zero, a small constraint may be added.

The Bernoulli model may be modified by setting $\eta_t(x)$ to now be a function of both $x_i$ and t:

$$p(y_i^{(t)}|x_i,z_i) = (1-\eta_t(x))^{|y_t^{(t)}-z_i|} \eta_t(x)^{1-|y_t^{(t)}-z_i|} \quad (3)$$

$\eta_t(x_i)$ is a function that represents the probability that annotator t is correct for example $x_i$. The resulting model thus takes into account the accuracy of annotators as it depends on specific examples.

$\eta_t(x)$ is set to be a logistic function:

$$\eta_t(x) = (1 + \exp(-w_t^T x_i - \gamma_t))^{-1} \quad (4)$$

In other words, the probability of being correct for each annotator is a sigmoidal function with parameters $w_t$ and $\gamma_t$. These parameters can be estimated from training data.

$p(z_i|x_i)$: One can set $p(z_i|x_i)$ to be any distribution or in this case classifier g: X→Z, which maps x to z. For simplicity, $p(z_i|x_i)$ is set to be the logistic regression model:

$$p(z_i=1|x_i) = (1 + \exp(-\alpha^T x_i - \beta))^{-1}. \quad (5)$$

The logistic model measures the probability of an event to occur. In classification problems, this can be the event that the data point is in a particular class. The logistic model can be obtained by fitting the data (i.e., learning) to a logistic curve. This model utilizes several predictor or input variables, a parameter $\alpha$ (normally a vector) and a parameter $\beta$ (a scalar).

In the above case, the classification problem is assumed binary, but one can easily extend this to multiple classes, e.g., using multiple logistic regression.

Given the probabilistic model, the set of all parameters, $\theta = \{\alpha, \beta, \{w_t\}, \{\gamma_t\}\}$ (i.e., the parameters of equations 2, 4 and 5), is estimated by maximizing the likelihood function. Equivalently $$\operatorname*{argmax}_{\theta} \prod_t \prod_i p(y_i^{(t)}|x_i;\theta), \quad (6)$$

which becomes the following problem after taking the logarithm and including the ground-truth variable z:

$$= \operatorname*{argmax}_{\theta} \sum_t \sum_i \log \sum_{z_t} p(y_i^{(t)}, z_i | x_i; \theta) \quad (7)$$

Since there are missing variables z, a standard approach to solve the maximum likelihood problem is to employ the expectation maximization (EM) algorithm. The EM algorithm includes the E-step and M-step as follows.

$$E\text{-Step: Compute } \tilde{p}(z_i) = p(z_i | x_i, y_i), \quad (8)$$

$$\tilde{p}(z_i) \propto p(z_i, y_i | x_i)$$

$$= \prod_t p(y_i^{(t)} | x_i, z_i) p(z_i | x_i)$$

M-step: Maximize $\Sigma_t \Sigma_i E_{\tilde{p}(z_i)}[\log p(y_i^{(t)}, z_i, x_i)]$. This optimization depends on the specific form of the conditional probabilities. In the formulations that follow, the update equations for the more general case where $\sigma_t(x)$ and $\eta_t(x)$ are both functions of the data $x_i$ and labeler t, are shown. Since, there is no closed-form solution for maximizing $\Sigma_t \Sigma_i E_{\tilde{p}(z_i)}[\log p(y_i^{(t)}, z_i, x_i)]$ with respect to the parameters, the LBFGS quasi-Newtown method (that does not require second order information) is applied to solve the following optimization problem:

$$\max_{\alpha,\beta,\{\gamma_t\},\{w_t\}} f_{opt}(\alpha, \beta, \{\gamma_t\}, \{w_t\}) = \max_{\alpha,\beta,\{\gamma_t\},\{w_t\}} \sum_{i,t} E_{\tilde{p}(z_t)} \begin{bmatrix} \log p(y_i^{(t)} | x_i, z_i) + \\ \log p(z_t, x_t) \end{bmatrix}$$

For convenience, the gradients with respect to the different parameters for the two candidate models (Gaussian or Bernoulli) are provided here:

$$\frac{\partial f_{opt}}{\partial \alpha} \propto \sum_i \frac{\Delta \tilde{p} \exp(-\alpha^T x - \beta) x}{(1 + \exp(-\alpha^T x - \beta))^2}$$

$$\frac{\partial f_{opt}}{\partial \beta} \propto \sum_i \frac{\Delta \tilde{p} \exp(-\alpha^T x - \beta) x}{(1 + \exp(-\alpha^T x - \beta))^2}$$

where $\Delta \tilde{p} = \tilde{p}(z_i = 1) - \tilde{p}(z_i = 0)$. When a Gaussian model is applied for $p(y_i^{(t)}|x_i, z_i)$:

$$\frac{\partial f_{opt}}{\partial \beta} = \frac{\left[y_i^{(t)^2} - \tilde{p}(z_i = 1)(2y_i^{(t)} - 1)\right]}{\sigma_t^3(x)} - \frac{1}{\sigma_t(x)}$$

When a Bernoulli model is applied for $p(y_i^{(t)}|x_i,z_i)$:

$$\frac{\partial f_{opt}}{\partial \eta_t(x)} = (-1)^{y_t^{(t)}}(\tilde{p}(z_i=0) - \tilde{p}(z_i=1))$$

$$\frac{\partial \eta_t(x)}{\partial w_t} = \frac{\partial \sigma_t(x)}{\partial w_t}$$

$$= \frac{\exp(-w_t^T x_t - \gamma_t)x_i}{(1+\exp(-w_t^T x_i - \gamma_t))^2}$$

$$= \sigma_t(x)(1-\sigma_t(x))x_i, \text{ for the Gaussian model} \quad (9)$$

$$= \eta_t(x)(1-\eta_t(x))x_i, \text{ for the Bernoulli model} \quad (10)$$

$$\frac{\partial \eta_t(x)}{\partial \gamma_t} = \frac{\partial \sigma_t(x)}{\partial \gamma_t}$$

$$= \frac{\exp(-w_t^T x_i - \gamma_t)}{(1+\exp(-w_t^T x_i - \gamma_t))^2}$$

$$= \sigma_t(x)(1-\sigma_t(x)), \text{ for the Gaussian model} \quad (11)$$

$$= \eta_t(x)(1-\eta_t(x)), \text{ for the Bernoulli model} \quad (12)$$

To learn the parameters α, β, $\{\gamma_t\},\{w_t\}$, and obtain a distribution over the missing variables $z_t$, iterate between the E and M steps until convergence. The method is summarized in Algorithm 1:

---
[Algorithm 1]
---
input: X,Y : set: α = 0, β = 0 and threshold ε
initialize: $α_{new}, β_{new}, w_t$ and $γ_t$
while: $||α - α_{new}||^2 + (β - β_{new})^2 \geq ε$ do
   E-step: estimating $\tilde{p}(z)$ by using equation (8)
   M-step: updating $α_{new}, β_{new}, w_t$ and $γ_t$ that
   maximize $\Sigma_t \Sigma_i E_{\tilde{p}(z_i)}[\log p(y_i^{(t)}, z_i | x_i)]$ using the
   LBFGS quasi-Newton approximation to compute
   the step, with gradient equations (9-12).
end while
return α, β, $\{w_t\}, \{γ_t\}$
---

Once the parameters α,β have been estimated in the learning stage, the probabilistic model's construction is complete and the built model can be executed and used to produce labeler error/accuracy estimates and classify new data points (130). For example, a new data point x can be classified by letting $p(z=1|x)=(1+\exp(-α^T x-β))^{-1}$ where z=1 is the class label of interest.

Alternatively, for a new data point x we could request an annotator to provide the label. The functions $\eta_t(x)$ and/or $\sigma_t(x)$ can be used to determine the appropriate labeler (e.g., the most accurate labeler or the most consistent labeler). For example, for each annotator t=1, 2, . . . T , calculate their corresponding estimated accuracy (e.g., probability of being correct) for the known data point x: $\eta_1(x), \eta_2(x), \ldots, \eta_T(x)$, and request the annotator with the largest accuracy for the data point to annotate the data point. Similarly, we could use this same idea and utilize $\sigma_t(x)$ instead of $\eta_t(x)$. In this case, if we want to choose the annotator with the lowest error variance, calculate each annotator's estimated error and pick the annotator for which $\sigma_t(x)$ is smallest. In some cases, we may want to request annotations from the best K annotators (other choices are also possible depending on the task at hand).

Figure 3:
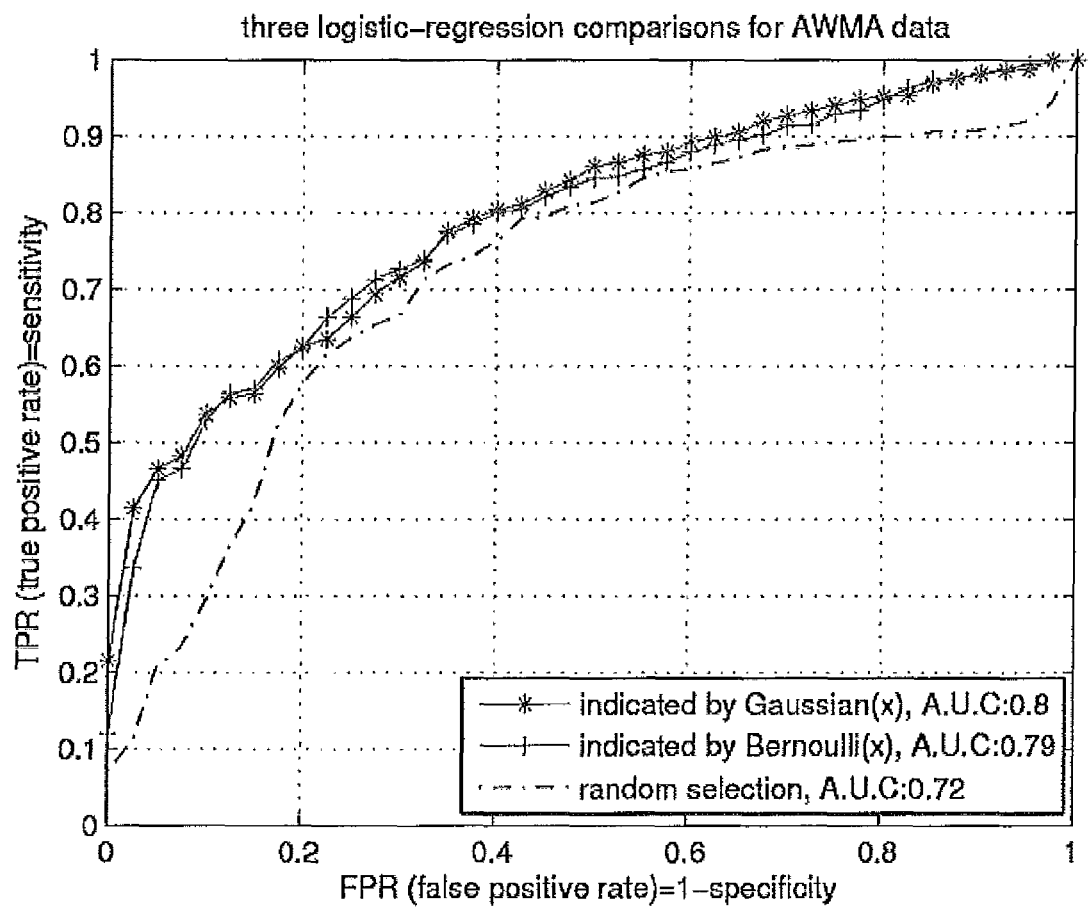
FIG. 3 is a comparison of a probabilistic model according to exemplary embodiments of the present invention to a baseline model.

In FIG. 3, we show that the procedure just described outperforms an alternative procedure consisting of randomly selecting any of the annotator (e.g., radiologists), FIG. 3 shows that the area under the ROC curve is larger (e.g., better) if we follow the procedure just described. The Gaussian and Bernoulli curves correspond to picking the annotator with the lower $\sigma_t(x)$ and larger $\eta_t(x)$, respectively, given the data point (x) to be labeled.

Given the probabilistic model introduced so far, the following describes its properties and additional uses.

To simplify the presentation, the set notation $\{y^{(t)}\}$ is used as shorthand for $\{y^{(t)}\}_{t=1}^T = \{y^{(1)}, \ldots, y^{(T)}\}$ and as shorthand for $\{y^{(t)}\}_{t=1, t \neq k}^T$.

It may be interesting to ask what the model is actually doing in order to estimate the ground truth from the information provided by all the labelers. One way to answer this question is by analyzing the posterior distribution $p(z|\{y^{(t)}\}, x)$, which is given by:

$$p(z|\{y^{(t)}\}, x) = p(\{y^{(t)}\}|z,x)p(z|x)/p(\{y^{(t)}\}|x) \quad (13)$$

$$= \frac{\prod_t p(y^{(t)}|z,x)p(z|x)}{\sum_z \prod_t p(y^{(t)}|z,x)p(z|x)}$$

If the log-likelihood ratio $$LLR(\{y^{(t)}\}, x) = \log \frac{p(z=1|\{y^{(t)}\}, x)}{p(z=0|\{y^{(t)}\}, x)}$$

is considered for the Bernoulli case, the following is obtained:

$$LLR = \text{log}it[p(z=1|x)] + \sum_t (-1)^{(1-y^{(t)})} \text{log}it[\eta_t(x)] \quad (14)$$

$$= α^T x + β + \sum_t (-1)^{(1-y^{(t)})} w_t^T x + γ_t,$$

where log it(p)=p/1−p. This provides the insight that the classification boundary depends on a linear combination of a score provided by the learned model with parameters (α, β) and the signed contributions from the T individual annotators. The annotator contributions are given by the annotator specific (linear) model of expertise, weighted positively or negatively depending on the label provided (1 or 0 respectively). Note that with a few notation changes this final form can be written as a logistic regression classifier as well.

For the Gaussian case, the regression becomes:

$$LLR = \text{log}it[p(z=1|z)] + \sum_t (-1)^{(1-y^{(t)})} \frac{1}{\sigma_t(x)} \quad (15)$$

$$= α^T x + β + T^+ - T^- + \sum_t (-1)^{(1-y^{(t)})} \exp(-w_t^T x - γ_t),$$

where $T^+$ and $T^-$ are the counts of positive and negative labels respectively. Similarly to the case above, the solution involves a linear combination of scores given by each labeler. In this case the score is calculated using the exponential function.

From equation 13 the posterior can be derived when not all the annotators provided a label for a data point by computing the appropriate marginal distributions. If annotator k was missing, one can show that the model provides a simple solution:

$$p(z\mid\{y^{t/k}\}, x) = \frac{\prod_{t/k} p(y^{(t)}\mid z, x) p(z\mid x)}{\sum_z \prod_{t/k} p(y^{(t)}\mid z, x) p(z\mid x)}, \quad (16)$$

which basically ignores the missing annotator. This implies the natural result that if all annotators are missing, equation 5 is obtained.

The presented model provides an expression for estimating the ground-truth even purely from the observed annotations (when the input data has not been observed):

$$p(z\mid\{y^{(t)}\}) = \int \prod_t p(y^{(t)}\mid z, x) p(z\mid x) d\, p(x) \quad (17)$$

Since there is no direct prior p(x), sampling can be relied on. One option is to use the previously seen cases (training data) as a good sample for X. Let $X_s = \{x_1, x_2, \ldots, x_s\}$, be a sample from the random variable X. This sample can be used to compute the posterior by:

$$p(z\mid\{y^{(t)}\}) \approx \frac{1}{S}\sum_{s=1}^{S} p(z\mid x_s)\prod_t p(y^{(t)}\mid z, x_s) \quad (18)$$

which can be done easily given a learned model.

If the ground-truth (for a particular data point) is known, the annotator accuracy can be straightforwardly evaluated. However, this is not the usual case. For example, what if we do not have the ground-truth (it does not exist or is expensive to obtain)? The approach provides a way to evaluate an annotator even without reliance on ground-truth. This can be done by evaluating the following conditional distribution:

$$p(y^{(k)}\mid\{y^{(t/k)}\}, x) = \frac{p(\{y^{(t)}\}\mid x)}{p(\{y^{(t/k)}\}\mid x)} \quad (19)$$

$$= \frac{\sum_z p(\{y^{(t)}\}\mid z, x) p(z\mid x)}{\sum_z p(\{y^{(t/k)}\}\mid z, x) p(z\mid x)}$$

Note that if the ground-truth is given (along with the input data), the annotators are mutually independent and $p(y^{(k)}\mid\{y^{t/k}\}, x) = p(y^{(k)}\mid z, x)$, as expected.

Figure 4:
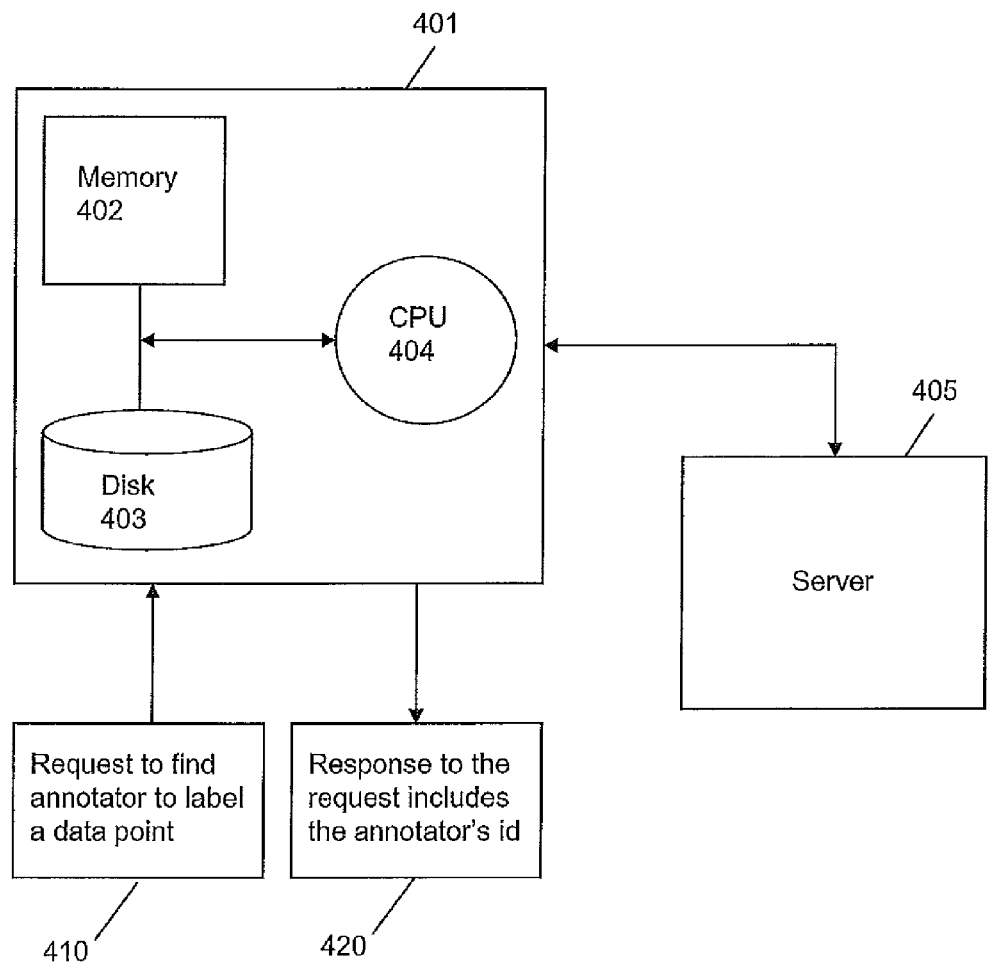
FIG. 4 is a computer system in which an exemplary embodiment of the present invention may be implemented.

An exemplary embodiment of the present invention will now be described with reference to apparatus 401 in FIG. 4. The apparatus 401, which may be a computer, includes a memory 402, a disk 403, and a processor such as a central processing unit (CPU) 404. The apparatus 401 may be connected to a server 405 via a wired or wireless network. The server 405 may be a local or remote data server containing training data (e.g., MR or CT images or medical transcripts) to build a probabilistic model according to an exemplary embodiment of the present invention. The server 405 could also be a network server (e.g., web server) utilized to obtain a request to select the most appropriate annotator and to be given or give the response about which annotator is most appropriate.

It is to be understood that the term "processor" as used herein is intended to include any processing device, such as, for example, one that includes a CPU and/or other forms of processing circuitry. Further, the term "processor" may refer to more than one individual processor. The term "memory" is intended include memory associated with a processor or CPU, such as, for example, random access memory (RAM), read only memory (ROM), a fixed memory device (for example, hard drive), a removable memory device (for example, diskette), a flash memory and the like. In addition, the phrase "input and/or output interface" as used herein, is intended to include, for example, one or more mechanisms for inputting data to the processing unit (for example, mouse), and one or more mechanisms for providing results associated with the processing unit (for example, printer).

In some embodiments, a request 410 to find the best annotator (e.g., doctor, some other medical expert or non-expert) to label a particular data point may be input to apparatus 401. For example, a user might want to find the best person available to label MR lung images. The apparatus 401 may then find the identity of the best annotator using at least one the processes described above. In some embodiments, a response 420 to the request is output from the apparatus 401. The response 420 may included the annotator's id. In other embodiments, the user may want to know if certain areas of the MR lung images are cancerous. The user could then configure the request 410 as such. The apparatus 401 would then classify the areas on the MR lung images as cancerous or not using at least one of the processes described above. In this case, the response 420 would include the classified data.

In summary, exemplary embodiments of the present invention consist of a process of building a mathematical/probabilistic model to predict the label of a data point. The model is built from labels provided by multiple annotators. The model considers the different characteristics of the annotators, and thus, annotator specific parameters are part of the model and estimated from (the training/observed) data. The label that each annotator assigns to a data point depends both on the unknown true label of the data point and the characteristics of the data point itself. The model can then be used to select which annotator is the most appropriate (e.g., the best) to annotate/label a given new data point.

In an exemplary embodiment, the present invention may be implemented in software as an application program tangibly embodied on a program storage device (e.g., magnetic floppy disk, RAM, compact disk read (CD) ROM, digital video disk (DVD), ROM, and flash memory). The application program may be uploaded to, and executed by, a machine comprising any suitable architecture.

It is to be understood that because some of the constituent system components and method steps depicted in the accompanying figures may be implemented in software, the actual connections between the system components (or the process steps) may differ depending on the manner in which the present invention is programmed. Given the teachings of the present invention provided herein, one of ordinary skill in the art will be able to contemplate these and similar implementations or configurations of the present invention.

While the present invention has been described in detail with reference to exemplary embodiments thereof, those skilled in the art will appreciate that various modifications and substitutions can be made thereto without departing from the spirit and scope of the present invention as set forth in the appended claims.

What is claimed is:

1. A method, comprising:
   receiving multi-labeler data that includes data points labeled by a plurality of labelers;
   building a model from the multi-labeler data, wherein the model includes an input variable that corresponds to the data points, a label variable that corresponds to true labels for the data points, and variables for the labels given by the labelers, wherein the variables for the labels given by the labelers for a particular data point depend on the input variable that corresponds to that data point and the label variable that corresponds to the true label for that data point; and
   executing the model, in response to receiving new data points, to determine a level of expertise of the labelers for the new data points,
   wherein the method is performed using a processor.

2. The method of claim 1, further comprising assigning the new data points to a particular labeler for labeling based on the labeler's level of expertise.

3. The method of claim 2, wherein the labeler with the highest level of expertise is selected for the labeling of the new data points and wherein the highest level of expertise corresponds to the labeler's estimated ability to label the new data points more accurately than the other labelers.

4. The method of claim 1, further comprising classifying the new data points.

5. The method of claim 4, wherein a new data point is classified by using less than all of the labels provided by the labelers.

6. The method of claim 4, wherein the new data points are classified using a classifier, wherein the labels provided by the labelers are the only labels input to the classifier.

7. The method of claim 1, wherein the labelers include radiologists and the multi-labeler data includes radiological images.

8. The method of claim 7, wherein the data points correspond to information extracted from regions of the images, the image regions including lesions, abnormalities or other elements of interest for patient treatment or diagnosis.

9. The method of claim 1, wherein the labelers include medical experts and the multi-labeler data includes medical transcripts.

10. The method of claim 9, wherein the data points correspond to information extracted from a medical transcript, the information including medical events, diagnosis, procedures underwent and overall state for a patient.

11. A system, comprising:
    a memory device for storing a program;
    a processor in communication with the memory device, the processor operative with the program to:
    receive multi-labeler data that includes data points labeled by a plurality of labelers;
    build a model from the multi-labeler data, wherein the model includes an input variable x that corresponds to the data points, a label variable z that corresponds to true labels for the data points, and variables for the labels y given by each labeler t; and
    execute the model, in response to receiving new data points, to determine a level of expertise of the labelers for the new data points,
    wherein the model is represented by, $$p(Y, Z \mid X) = \prod_i p(z_i \mid x_i) \prod_i p(y_i^{(t)} \mid x_i, z_i),$$

where $p(z_i, x_i)$ is a classifier for classifying new data points, and $p(y_i^{(t)} \mid x_i, z_i)$ is an error/accuracy estimator for determining labeler expertise.

12. The system of claim 11, wherein $p(y_i^{(t)} \mid x_i, z_i)$ is represented by $p(y_i^{(t)} \mid x_i, z_i) = N(y_i^{(t)}; z_i, \sigma_t(x_i))$, wherein N is the number of data points input to the model and $\sigma_t(x)$ is an estimated error of a labeler for a particular data point.

13. The system of claim 12, wherein a $\sigma_t(x)$ is represented by $\sigma_t(x) = (1+\exp(-w_t^T x_t - \gamma_t))^{-1}$, wherein w is a vector and $\gamma$ is a scalar.

14. The system of claim 11, wherein $p(y_i^{(t)} \mid x_i, z_i)$ is represented by $p(y_i^{(t)} \mid x_i, z_i) = (1-\eta_t(x))^{|y_t^{(t)} - z_t|} \eta_t(x)^{1-|y_t^{(t)} - z_t|}$, wherein $\eta_t(x)$ is an estimated accuracy of a labeler for a particular data point.

15. The system of claim 14, $\eta_t(x)$ is represented by $\eta_t(x) = (1+\exp(-w_t^T x_t - \gamma_t))^{-1}$, wherein w is a vector and $\gamma$ is a scalar.

16. The system of claim 11, wherein $p(z_i, x_i)$ is represented by $p(z_i=1 \mid x_i) = (1+\exp(-\alpha^T x_i - \beta))^{-1}$, wherein $\alpha^T$ is a vector and $\beta$ is a scalar.

17. A computer program product, comprising:
    a non-transitory computer readable storage medium having computer readable program code embodied therewith, the computer readable program code comprising:
    computer readable program code configured to perform the steps of:
    receiving multi-labeler data that includes data points labeled by a plurality of labelers;
    building a model from the multi-labeler data, wherein the model includes an input variable that corresponds to the data points, a label variable that corresponds to true labels for the data points, and variables for the labels given by each labeler, wherein the variables for the labels given by the labelers for a particular data point depend on the input variable that corresponds to that data point and the label variable that corresponds to the true label for that data point;
    receiving new data points; and
    classifying the new data points using the model.

* * * * *